US006976387B2

(12) United States Patent
Anthe et al.

(10) Patent No.: US 6,976,387 B2
(45) Date of Patent: Dec. 20, 2005

(54) HARDNESS MEASURING DEVICE COMPRISING A HOUSING AND A PENETRATION BODY IN PARTICULAR A MANUAL DEVICE

(75) Inventors: Enno Anthe, Bornheim-Sechtem (DE); Werner Lammerich, Siegburg (DE)

(73) Assignee: Agfa NDT GmbH, (DE)

( * ) Notice: Subject to any disclaimer, the term of this patent is extended or adjusted under 35 U.S.C. 154(b) by 0 days.

(21) Appl. No.: 10/499,594

(22) PCT Filed: Sep. 30, 2002

(86) PCT No.: PCT/DE02/03682

§ 371 (c)(1),
(2), (4) Date: Jun. 17, 2004

(87) PCT Pub. No.: WO03/056303

PCT Pub. Date: Jul. 10, 2003

(65) Prior Publication Data
US 2005/0016264 A1 Jan. 27, 2005

(30) Foreign Application Priority Data
Dec. 21, 2001 (DE) ............................... 101 63 656

(51) Int. Cl.⁷ ........................... G01N 3/00; G01N 3/30; G01N 3/32; G01N 3/08; G01M 7/00
(52) U.S. Cl. .............................. 73/83; 73/85; 73/12.04
(58) Field of Search ....................... 73/82, 85, 12.01, 73/12.04, 12.13, 12.09, 573

(56) References Cited

U.S. PATENT DOCUMENTS

| | | | | |
|---|---|---|---|---|
| 3,879,982 A | * | 4/1975 | Schmidt | 73/79 |
| 4,411,153 A | * | 10/1983 | Lewis | 73/79 |
| 4,640,120 A | * | 2/1987 | Garritano et al. | 73/12.13 |
| 4,646,571 A | * | 3/1987 | Kising et al. | 73/573 |
| 5,497,649 A | * | 3/1996 | Ambur et al. | 73/12.06 |
| 5,616,857 A | * | 4/1997 | Merck et al. | 73/82 |
| 5,739,411 A | * | 4/1998 | Lee et al. | 73/12.13 |

* cited by examiner

Primary Examiner—Hezron Williams
Assistant Examiner—Tamiko Bellamy
(74) Attorney, Agent, or Firm—Cantor Colburn LLP

(57) ABSTRACT

The hardness measuring device (18) is provided with a) a penetration body (20), which penetrates a workpiece (28) along a penetration vector (58) during a measuring process, b) a housing (30) which embodies a guide track (32) for the penetration body (20) which moves along said guide track (32) between a rest position and a measuring position and with a mechanical drive (spring 40, 62), which engages with the penetration body (20), at least in the rest position and which fixes the test force or the test impulse for a measuring process and c) an electronic control circuit (48), which controls the measuring process and which determines a hardness value from the movement and/or the penetration action of the penetration body (20) into the workpiece (20). The hardness measuring device (18) comprises an acceleration sensor (54), which produces an angular signal, depending on the angle which the penetration vector (58) makes with the local gravitational vector (56). The angular signal is supplied to the control circuit (48), which, on taking into account the known mass of the penetration body (20) and parts connected thereto, calculates a correction value for a precise hardness measurement.

13 Claims, 4 Drawing Sheets

Figure 1:
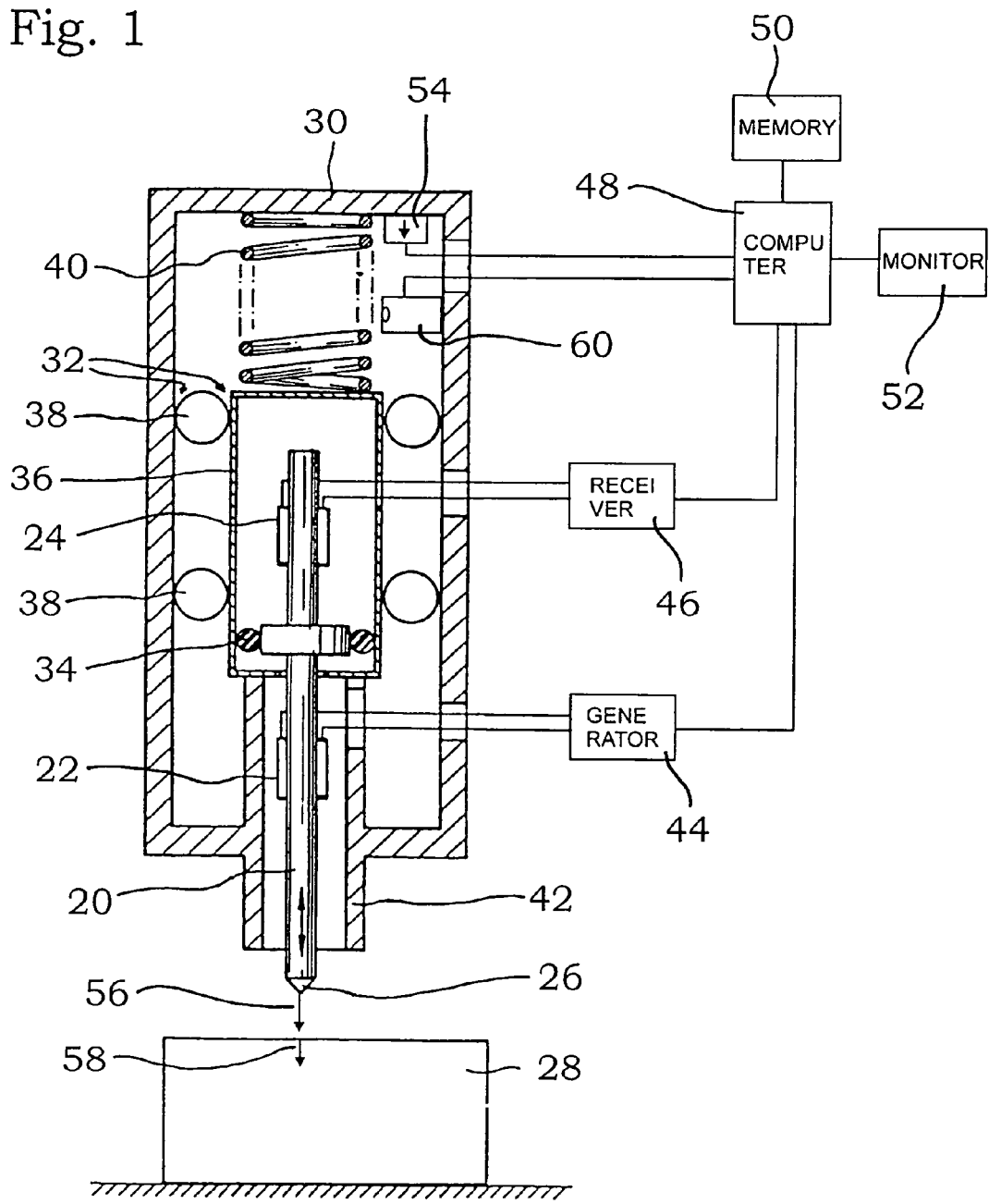

HARDNESS MEASURING DEVICE COMPRISING A HOUSING AND A PENETRATION BODY IN PARTICULAR A MANUAL DEVICE

The invention relates to a hardness measuring device having a penetration body which penetrates a workpiece along a penetration vector during a measuring process, a housing which embodies a guide track for the penetration body which moves along said guide track between an at rest position and a measuring position and which further comprises a mechanical drive which engages the penetration body at least in the at rest position and which fixes either the test force or the test impulse during a measuring process and an electronic control circuit which controls the measuring process and which determines a hardness value from the movement and/or the penetration behavior of the penetration body into the workpiece.

The current state of the art describes several hardness measuring devices that are implemented in accordance with the features of the first paragraph and which will be discussed in closer detail herein after. In principle, these devices may be divided into two different classes, namely devices for dynamic hardness testing on the one hand and devices for static hardness testing on the other hand.

Devices for dynamic hardness testing in which the penetration body is caused to move in a pulse-like manner toward the workpiece to be tested are known from U.S. Pat. No. 4,411,153, U.S. Pat. No. 3,879,982, U.S. Pat. No. 5,176,026, DE 24 52 880 A and PCT/DE 96/00563. At the end of its stroke toward the workpiece, the penetration body strikes said workpiece prior to rebounding therefrom and performing its return stroke. The momentum of the penetration body, more specifically its velocity, is sensed, preferably by a contactless sensing method, both during the advance and the return stroke. The extent of hardness of the workpiece is obtained from the difference between the momentum of the advance stroke and that of the return stroke. In these-devices, the mechanical drive mostly is a quick acting spring that temporarily accelerates the penetration body. After the acceleration phase the quick acting spring is no longer operative, the penetration body still moving a distance without being accelerated before striking the workpiece.

In the static or the quasi-static hardness measuring devices as they are known for example from U.S. Pat. No. 3,572,097; U.S. Pat. No. 4,646,571; U.S. Pat. No. 5,092,175 and DE 198 12 026 A, a tension or compression spring is permanently provided between housing and penetration body. The penetration tip of the penetration body protrudes from the housing. Said tip is applied to one contact point on the workpiece to be tested. Now, the test force is exerted in that the housing is pushed toward the contact point, meaning in that the spring is tensioned. Once a certain spring travel has been reached, the test force is achieved and the hardness measurement can be performed.

With regard to hardness measuring methods, reference is also made to DIN 50359.

The drawback to these and similar hardness measuring devices is as follows: The hardness measuring devices can be applied to a workpiece with different orientations relative to the gravitational vector. It is for example possible to work in reverse in which case the operation is performed exactly counter to the direction of the gravitational vector. The device may be applied to the side, meaning approximately transverse to the gravitational vector and so on. The term gravitational vector is to be construed as a unit vector which, taking departure from the contact point, indicates the direction of the gravity field, i.e., is generally directed toward the center of the earth.

The penetration body has a mass of its own. It is at least or typically on the order of some grams. If the penetration body penetrates along the penetration vector parallel to the gravitational vector, the mass positively contributes to the test force (in the case of more or less static hardness measuring methods) or to the impulse (in the case of dynamic hardness measuring methods). If, by contrast, measurement is carried out in reverse, meaning if the penetration vector is antiparallel to the gravitational vector, the mass of the penetration body reduces the test force or the impulse respectively. Intermediate positions will cause intermediate situations to occur. The mass of parts that are rigidly connected to the penetration body and the friction of the penetration body along its guide track are also to be taken into consideration. Finally, in static measuring methods, the contribution of the mass of a compression spring is also to be taken into consideration.

It is known in principle that the direction in which a measuring device of the type mentioned herein above is applied influences the impulse of the penetration body. Hardness measuring devices manufactured according to the document DE 198 12 026 A mentioned come with a correction table. When a test is being performed, the angle between penetration vector and gravitational vector must be estimated or determined. Then, it is possible to consult the table as to how the hardness value displayed by the electronic control circuit of the device is to be manually corrected. Although this permits to take into consideration the influence of gravity, the method in itself is complicated, time-consuming and not always very accurate.

With the hardness measuring device in accordance with PCT/DE 96/00563, the momentum of the penetration body is measured at two sites at least, both on the advance and on the return stroke. This permits to automatically take into consideration the influence of gravity onto the movement of the penetration body.

This is where the invention comes to bear. It is the object of this invention to indicate a largely universally utilizable add-on unit to a hardness measuring device of the type mentioned herein above by means of which a correction value for a measured hardness value is automatically obtained. Preferably, the hardness measurement is performed being right away adjusted by the correction value and/or the hardness result first obtained independent of gravity is adjusted and displayed in its corrected form.

This object is solved by the hardness measuring device having the features of claim 1.

The solution of the invention is particularly suited for use in handheld devices, meaning in devices that are of small construction and, as a result thereof, universally utilizable on any site. In a first step, correction is made by automatically determining the angle between the penetration vector and the gravitational vector. The acceleration sensor is used for this purpose. Components indicating the angular position between an axis of the device and the gravitational vector are available in commerce. Such type components are used in accordance with the present invention. The acceleration sensor outputs an angular signal.

In a second step, the angle that has been determined is automatically associated with a correction value. This can be achieved either by computation or by resorting to a stored table. Then, a) the test force or the impulse respectively are preferably immediately adjusted by the correction value. For this purpose, when using a static measuring method, the force present in the tension or compression spring and depending on the respective deflection is determined and that force is selected which, in combination with the correction value, yields the desired test force. If dynamic measuring methods are being used, the quick acting spring is influenced such that the penetration body strikes the surface of the workpiece with always the same impulse. Accordingly, if measurement is to be performed parallel to the gravitational vector, the quick acting spring is adjusted to be weaker whereas, if measurement is performed antiparallel to the gravitational vector, the quick acting spring is adjusted to be stronger. Other terms used for designating a quick acting spring are accelerating spring and impulse spring.

Another possibility is to b) determine the respective hardness value and to then adjust it by the correction value according to the position of the hardness measuring device in the gravity field. In dynamic measuring methods for example, the penetration body, if it is oriented parallel to the gravitational vector, strikes the workpiece with an altogether higher impulse than if it were oriented antiparallel. Generally, the hardness value delivered is dependable because it has been corrected.

The solution in accordance with the invention is suited for all the hardness measuring devices of the type mentioned herein above. Accordingly, it is not only utilizable for dynamic hardness testing devices in particular, which is for example the case with the hardness testing device according to PCT/DE 96/00563.

The hardness measuring device is preferably configured as a handheld device. It is shaped like a pencil and may be conveniently grasped and operated by one hand. The invention is particularly useful in such type handheld apparatus that are carried to the application's site. Then, the hardness measurement is not performed in a laboratory.

Figure 2:
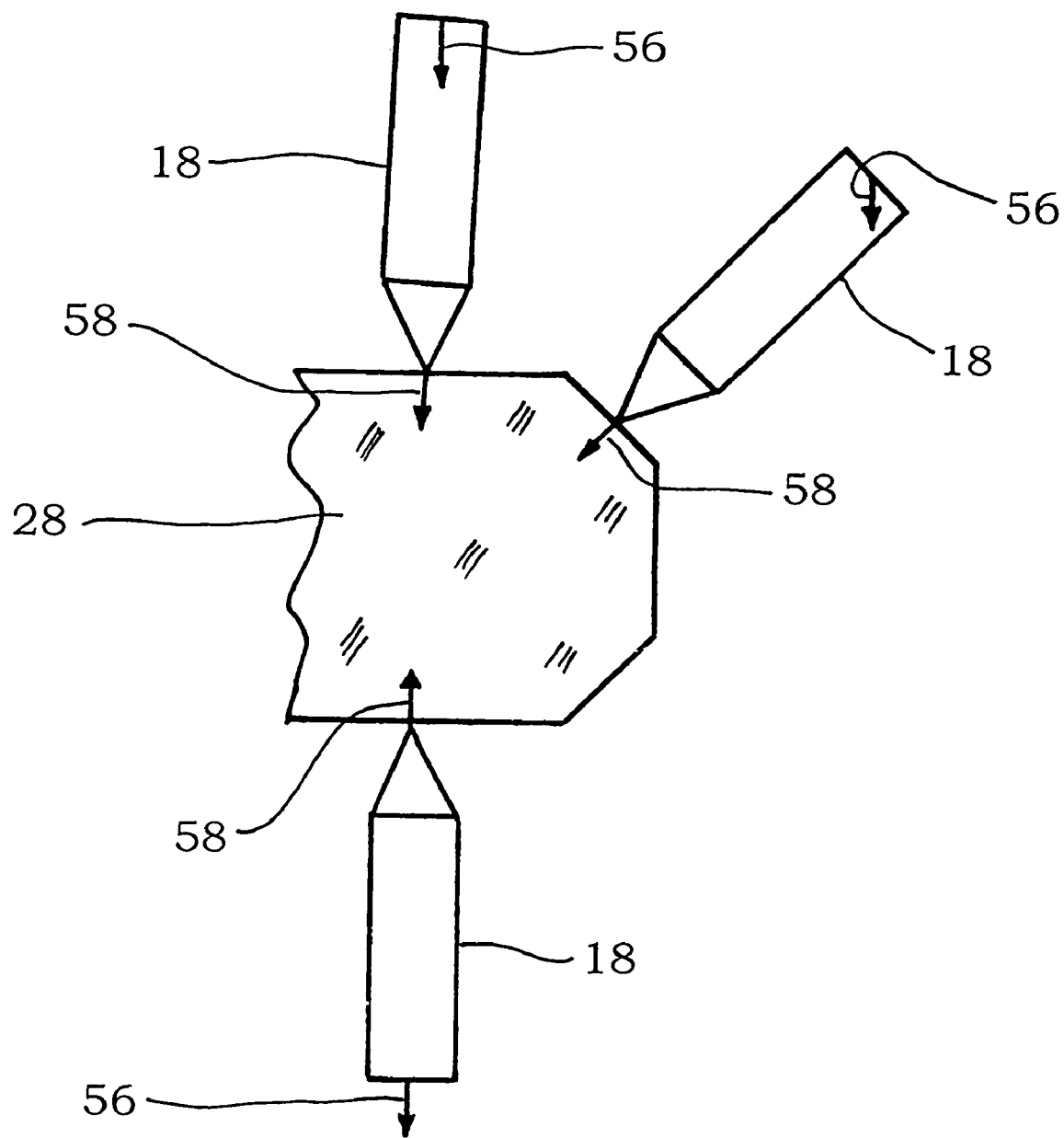
Figure 3:
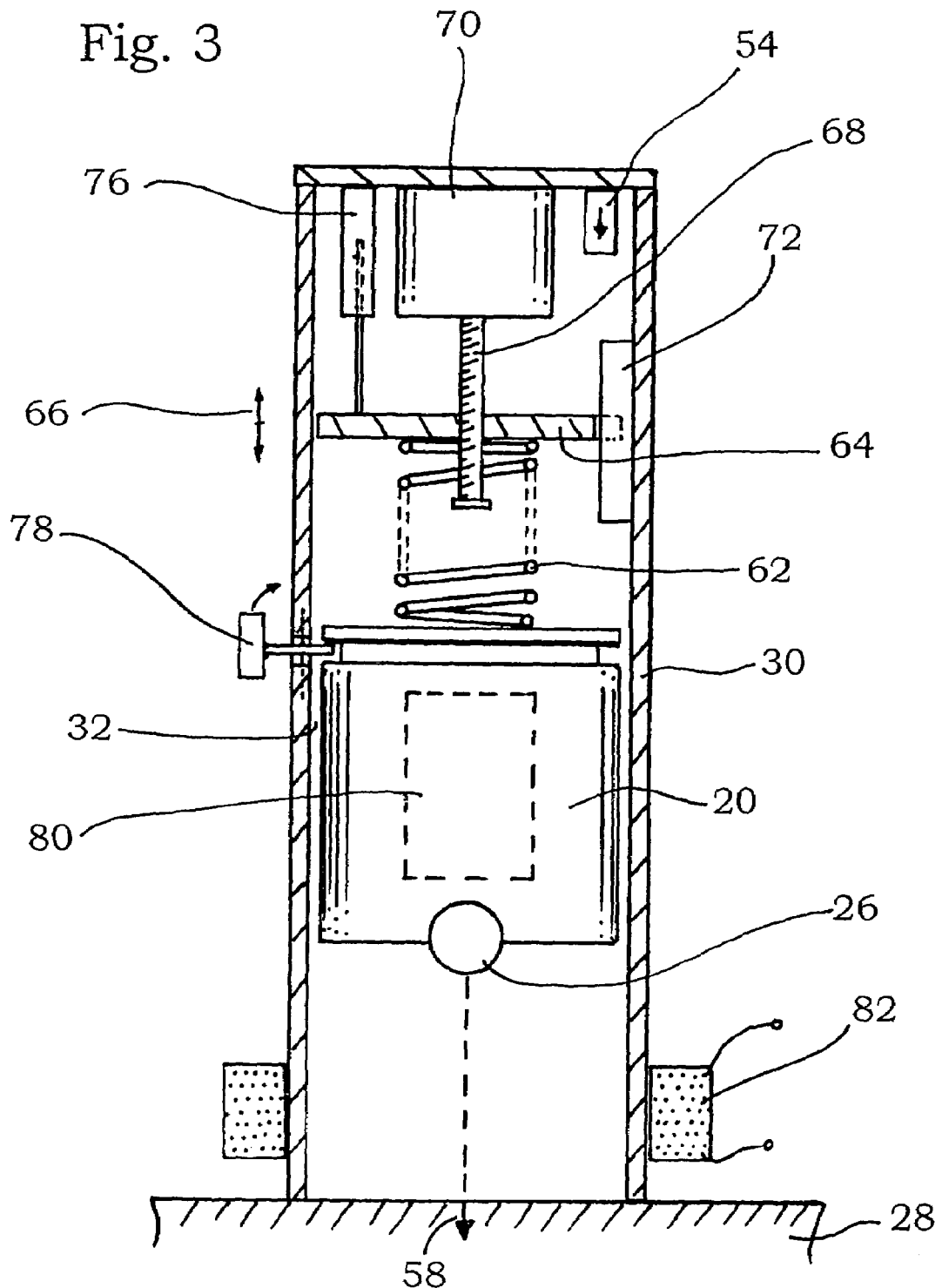
Figure 4:
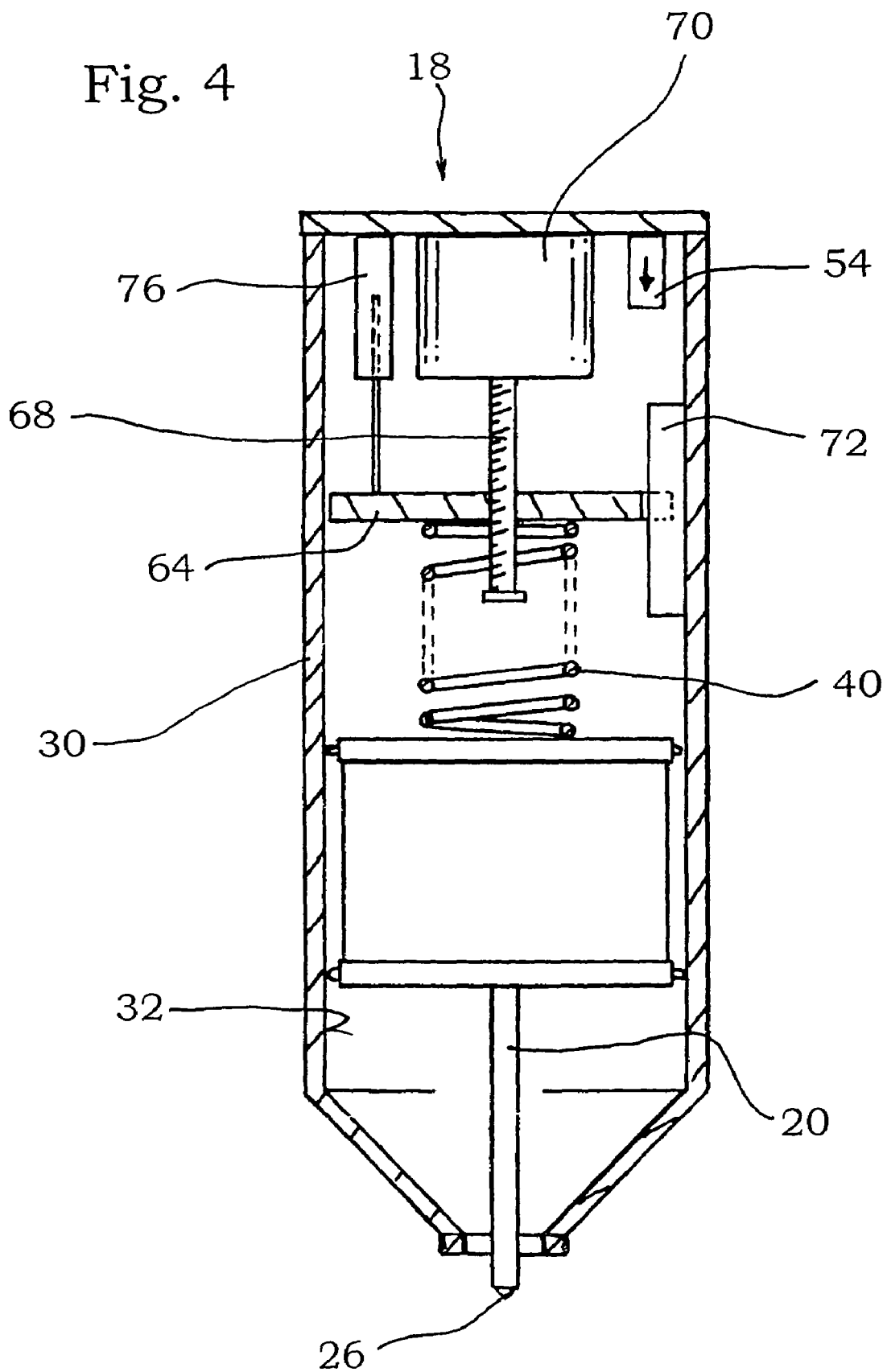

Further advantages and characteristics of the invention will become more apparent upon reading the claims and the following description of exemplary embodiments thereof with reference to the drawings in which:

FIG. 1 is a sectional view of a hardness measuring device that relies for operation on the UCI-method and is configured in accordance with the present invention, said device being located above a workpiece, FIG. 2 is an illustration showing three hardness measuring devices applied to a workpiece in different orientations relative to the gravitational vector, FIG. 3 is a sectional view similar to FIG. 1 of a dynamic hardness measuring device and FIG. 4 is a sectional view of a hardness measuring device equipped with a servomotor.

The hardness measuring device of FIG. 1 is a developed implementation of the hardness measuring device described in U.S. Pat. No. 4,646,571. This patent is incorporated herein by reference.

The hardness measuring device has a penetration body 20 which is configured here as a UCI-oscillating rod. Said rod is energized to oscillate through piezoelectric elements 22 that are connected thereto. The oscillations are sensed by piezoelectric elements 24 which are also connected to the penetration body 20. A penetration tip 26 is provided at its lower free end. During measurement, it comes into contact with a workpiece 28.

The penetration body 20 is substantially enclosed in a housing 30 configured to be in the shape of a pencil. At the lower free end thereof, a small portion of the penetration body 20 holding the penetration tip 26 protrudes from the housing. The housing 30 forms a guide track 32 for the penetration body 20. As the penetration body 20 is configured to be an oscillating rod, it cannot be guided directly. By means of elastic means 34, it is instead disposed in a holding part 36 that is for example bowl-shaped and moves with said rod. Through roller means 38, the holding part is positioned and guided opposite the inner wall of the housing 30. By a compression spring 40 that extends as a continuation of the rod-shaped penetration body 20, the holding part is in turn resting against the inner wall of the housing 30 that confronts the penetration tip 26. The compression spring urges the holding part 36 to come to rest against a tubular region 42 formed at the lower end region of the housing 30. The position shown in FIG. 1 is the at rest position.

The piezoelectric elements 22 are connected to a transmitter 44. The piezoelectric elements 24 are connected to a receiver 46. Both transmitter 44 and receiver 46 are connected to a control circuit 48 that is substantially configured to be a computer. Said control circuit in turn has a memory 50 to which it is connected and a monitor 52. Data may be entered into the control circuit 48 using a plug-in keyboard (not shown), said data being then stored in the memory 50. Thus, a desired test force such as a nominal test force or an elastic force Fe of the spring may for example be dictated.

An acceleration sensor 54 is solidly connected to the housing. An ADXL 105 type sensor of Analog Devices may be used for example. This sensor has a resolution of 2 mg (g=gravitational acceleration). The sensor is disposed so that, if the penetration body 20 is oriented parallel to the local gravitational vector 56, it displays 1 g. If it is rotated 180°, it displays −1 g. For a specific measurement, the local gravitational vector 56 is the unit vector that is directed from the penetration tip 26 toward the center of gravity of the earth.

Instead of the specific acceleration sensor mentioned, it is also possible to utilize a pendulum or a spherical body with a very off-centered mass that is mounted on gimbals. The respective condition is interrogated by suited means relying for operation on optical, magnetic or electromagnetic sensing methods.

During specific measurement, the penetration tip 26 comes into contact with the workpiece 28 which it penetrates. The direction of penetration is termed penetration vector 58. Said penetration vector 58 is assumed to be parallel to the elongated penetration body. In some application cases however, the longitudinal axis of the housing 30 and the penetration vector 58 may not coincide, not entirely at least.

During measurement, a test force is applied which is present in the form of a reaction force in the hand of a person using the hardness measuring device. During testing, the spring 40 is tensioned, it determines a fraction of the nominal test force. The other fraction is determined by the mass of the penetration body 20 and by the parts that are associated with the movements thereof, including a portion of the spring 40, and by the friction. Accordingly, the nominal test force is composed of a fraction provided by the mechanical drive, in the present case the compression spring 40, and of a fraction that is substantially provided by the mass of those parts that are directly involved in the measurement, more specifically the penetration body 20. The latter fraction may be positive and negative. It depends on the direction in the gravity field.

During measurement, the penetration body thus moves relative to the housing 30 along the guide track from the at rest position shown in FIG. 1 to a position for measurement that is given during measurement. An encoder 60 is provided within the housing 30 in the immediate neighborhood of the spring 40, said encoder sensing the deflection of the penetration body 20 from the at rest position shown in FIG. 1. It is configured to be a Hall probe. It senses each winding of the spring that moves in its immediate proximity. The encoder may be of other designs. It may for example be configured to be opto-electronic for scanning a bar code or it may be configured to be an inductive displacement encoder, and so on.

Both the encoder 60 and the acceleration sensor 54 are connected to the control circuit 48. As a result thereof, said circuit is informed of the condition of the spring 40, i.e., of the tension in the spring, and of the spatial position of the housing 30, in the present case by way of the angle between the penetration vector 58 and the gravitational vector 56. In FIG. 1, this angle is 0°.

When performing a hardness measurement, the user pushes the housing 30 of the hardness measuring device against the workpiece 28 until either a preset elastic spring force Fe or a nominal test force Fn is achieved. The two modes of operation are described herein after with reference to exemplary embodiment 1. At first, it will be described how to perform a test with an imposed nominal test force.

From the signal of the acceleration sensor 54 the control circuit 48 gains information as to the spatial position in which the penetration body 20 penetrates into the workpiece 28, that is as to the orientation of the penetration vector 58 relative to the gravitational vector 56. The mass of the moved parts in the hardness testing device is known and if not, it can be measured. This mass includes the mass of the penetration body 20 with its elements 22, 24, proportionately the electrical connecting lines, further the elastic means 34, the holding part 36, a fraction of the masses of the roller means 38 and a fraction of the mass of the spring 40. In orienting the measuring device of FIG. 1, this overall mass acts additively with the elastic force Fe present in the spring 40. If FIG. 1 were rotated 180° transverse to the plane of the drawing, the mass would have a subtractive effect. In the intermediate positions, the mass acts proportionately as a function of the angle, more specifically of the cosine of the angle.

In addition to the mass fraction, there also is the friction occurring in the region of the roller means 38. A small amount of the energy, i.e., force times distance, with which the housing 30 of the measuring device is moved toward the workpiece 28 is also converted into frictional heat.

In orienting the measuring device 18 parallel to the gravitational vector 56 as shown in FIG. 1, the forces due to the mass and the frictional forces, which will be referred to together herein after as secondary force Fo, add together to create the elastic force Fe of the spring 40. In order to achieve an imposed nominal force Fn, the elastic force Fe in the spring must therefore be smaller than with the measuring device being turned 180° for example.

If the device is constructed so as to keep the friction very low and if one neglects the dependency of the friction on the position in the gravity field, the following equality may be set up $$Fn = Fe + Fo * \cos alpha$$

wherein Fn=nominal force, Fe=elastically applied force, Fo=moved mass divided by g plus fraction of the frictional force and alpha=angle between the penetration vector 58 and the gravitational vector 56.

In the control circuit, the nominal force Fn is determined for each specific measuring process, meaning for each specific angle alpha. Measurement is performed such that the elastic force Fe increases from a small initial value. Once the increasing elastic force has reached the nominal test force Fn, the actual frequency of oscillation of the penetration body 20 is read, meaning a hardness measurement occurs.

The description made herein after will explain how to perform a test with an imposed elastic force Fe of the spring 40:

The test is run as described herein above. Measurement is initiated, that is the hardness measurement is performed, when the elastic force Fe in the spring 40 has reached a prescribed, preset value, independent of the spatial orientation of the hardness measuring device. A hardness value is obtained from the difference between the frequency of the oscillation and the initial condition. Subsequently, this value is corrected. For this purpose, the nominal force Fn associated with the elastic force Fe is computed according to the above formula, taking into consideration the angle alpha the measuring device makes with the gravitational vector 56. In the simplest approximation, the hardness value first obtained is multiplied by the quotient of Fn by Fe. In an improved implementation, a table stored in memory 50 is resorted to convert the value to the nominal hardness value. The latter is then displayed on the monitor 52.

FIG. 2 shows three hardness measuring devices 18 that are built according to the same principle and that are applied to a workpiece 28 in three different positions. The hardness measuring device 18 uppermost in the Fig. is applied almost parallel to the vertical direction, i.e., to the gravitational vector 56. The penetration vector 58 and the gravitational vector 56 are inclined to each other with a very small angle of about 3°. With the acceleration sensor having the resolution mentioned, a correction may be made with such small angles already.

A second hardness measuring device is applied at approximately a 45 degree angle to the vertical. Here, correction is already clearly noticeable and in any event considerably greater than in the first-mentioned case.

The third hardness measuring device 18 on the bottom of the figure is applied in reverse. Here, acceleration sensor 54 and penetration vector 58 are oriented in opposite directions, meaning they are oriented 180° relative to each other. In this case, the direction of the mass contribution of the penetration body 20, inclusive of the components associated therewith, is exactly counter to the direction of the orientation of FIG. 1. The friction conditions however are substantially the same as with the two vectors 56, 58 being parallelly oriented. By contrast, in the case of an inclined orientation, as is the case with the central measuring device which is oriented at a 45° angle, the angular dependence of the friction must generally be taken into consideration.

FIG. 3 shows an example of a device for dynamic hardness testing. The device has a substantially tubular housing 30 within which a penetration body 20 is capable of moving substantially freely along a guide track 32. The movement occurs along the path shown in a dashed line, which applies for both the advance and the return stroke. The penetration tip 26 is formed in a ball-shaped configuration.

The penetration body 20 is biased by a spring 62 which in the present case is configured to be a short compression spring. It is not connected to the penetration body 20 which it merely contacts. It is however connected to an adjusting plate that is slidable pursuant to the double-headed arrow 66. For this purpose, it is provided with a central thread through which engages a threaded rod 68. The threaded rod 68 is driven by an electric motor 70. The adjusting plate 64 is prevented from rotating by an abutment 72 engaging into a slot of the adjusting plate 64. The position of the adjusting plate 64 is sensed by a second encoder 76. There is provided an acceleration sensor 54.

The spring 62 is more or less biased, depending on the clear spacing between the adjusting plate 64 and the penetration body 20. In the at rest position of the measuring device shown, the penetration body 20 is secured by a pivotal pin that forms a release means 68. If an external region of the release means 68 is pivoted pursuant to the arrow, the penetration body 20 is released. It is caused to accelerate by spring 62 but, after a short distance, loses contact with said spring and is then free to fly the remaining distance. Its penetration tip 26 penetrates the workpiece 28 along the penetration vector 58. A hardness value is calculated from the difference between the momentum of the advance stroke and that of the return stroke.

The measuring device of FIG. 3 also permits to now adjust the bias of the quick acting spring 62 to the respective spatial orientation of the measuring device prior to releasing the pivotal pin 68. The motor is actuated until the bias in the acceleration spring plus the position-dependent contributions to the impulse yield a constant nominal impulse. Accordingly, if the measuring device, which is shown in FIG. 3 for arrangement with parallel vectors 56, 58, is desired to be utilized in the reverse position, meaning rotated 180°, the spring 62 needs to be more strongly biased to achieve the same nominal impulse, meaning the distance between the adjusting plate 64 and the penetration body 20 is to be reduced.

In a known manner, the measuring device has a magnet 70 which is disposed within the penetration body 20. Said magnet cooperates with an induction coil 72 which is disposed on the housing 30 outside thereof.

The measuring device of FIG. 3 may also be operated so that the force stored in the spring 62 is always the same. In this case, the motor will no longer directly compensate for the force of the spring when the measuring device is moved in space. The correction will be made subsequently, as was described herein above with reference to the quasi-static hardness measuring method.

Finally, FIG. 4 shows a hardness measuring device permitting to perform static hardness measurements. A spring 40, which in turn is implemented as a compression spring, is permanently connected to the adjusting plate 64 on the one hand and to the penetration body 20 on the other hand, meaning it will not come free from both.

This makes it different from the device of FIG. 3. Within the pencil-shaped housing 30, the penetration body 20 is slidable in the axial direction along a guide track 32, the friction is kept at the lowest possible level. At its lowermost end, the penetration body 20 has a penetration tip 26. FIG. 4 shows the at rest position. By the action of the spring 40, the penetration tip 26 is allowed to protrude freely to a certain extent from the lower, tapered end of housing 30.

The device of FIG. 4 can be operated in different modes which will be explained herein after.

In a first variant, the electric motor is not actuated during a measurement. During measurement, the penetration tip 26 is applied to a workpiece (not shown) and the housing 30 is pushed toward the contact point. This causes the spring 40 to be increasingly compressed until an elastic force Fe is achieved in which a measurement is performed. Since compression of the spring 40 causes the adjusting plate 64 to be deformed, the deflection of the spring may be determined by means of the encoder 76. Like in the exemplary embodiment shown in FIG. 1, a Hall probe may possibly be associated with spring 40. The signal of the acceleration sensor 54 corrects the measured value obtained depending on the position.

The measuring device of FIG. 4 may also be operated in such a manner that the spring 40 is compressed by the electric motor 70. After the penetration tip 26 has been applied to a workpiece, the motor 70 is actuated, which compresses the spring 40 so that the user feels a reaction force. Now the user no longer needs to apply on purpose the test force, he merely needs to react.

In another variant, upon achieving the prescribed elastic force Fe, which is associated with the desired nominal test force when the device is specifically spatially oriented, the motor 70 is driven and attracts the adjusting plate 64. The user of the device thus feels that the desired nominal test force is now achieved.

The outside dimensions of the housing 30 are chosen such that the housing can be held by one hand. Typically, the housing is substantially cylindrical and has a diameter of between 30 and 80 mm. The outer shell of the housing is configured to be a grip region.

What is claimed is:

1. A hardness measuring device comprising:
a penetration body that penetrates a workpiece along a penetration vector during a measuring process;
a housing, the housing comprises a guide track means for guiding the penetration body, the penetration body being moveable along the guide track means between a rest position and a measuring position, and the housing further comprises a mechanical drive that is in engagement with the penetration body at least in the rest position and the mechanical drive determines either a test force or a test impulse during a measuring process; and
an electronic control circuit that controls the measuring process and that calculates a hardness value from the movement and/or the penetration behavior into the workpiece of the penetration body,
wherein the hardness measuring device comprises an acceleration sensor, the acceleration sensor produces an angular signal, depending on the angle that the penetration vector makes with a local gravitational vector and the angular signal is input into the control circuit, the control circuit calculates a correction value for a precise hardness measurement, taking into consideration a known mass of the penetration body and of the parts connected thereto.

2. The hardness measuring device of claim 1, wherein the hardness measuring device is a handheld device and a grip region is provided on the housing, the grip region permitting the housing to be gripped in one hand.

3. The hardness measuring device of claim 1, wherein the mechanical drive comprises a spring that rests against the housing at one end of the spring and is disposed on the penetration body at the other end of the spring, the test force with which the penetration body is pressed into the workpiece substantially corresponds to a force with which the spring is compressed and the penetration body freely protrudes from the housing in the rest position and in the measuring position.

4. The hardness measuring device of claim 1, wherein the mechanical drive is an impulse spring that accelerates the penetration body when a measuring process is being initiated, the penetration body strikes the workpiece with an impulse when a measuring process is performed.

5. The hardness measuring device of claim 1, wherein the mechanical drive is a motor, and the motor is disposed between the housing and the penetration body.

6. The hardness measuring device of claim 3, further comprising an encoder that senses a displacement of the penetration body relative to the housing.

7. The hardness measuring device of claim 3, wherein a measuring process is initiated when the elastic force that biases the spring and the force the penetration body exerts onto the workpiece due to the mass of the penetration body added together yield a predetermined value, e.g., the nominal test force.

8. The hardness measuring device of claim 7, wherein a mechanical release means is provided that releases the spring when the nominal test force has been achieved.

9. The hardness measuring device of claim 1, wherein the control circuit comprises a memory that stores a listing of values comprising the mass of the penetration body that contributes to the test force, as a function of the angle the penetration vector makes with the gravitational vector, and the friction of the penetration body along its guide track that contributes to the test force, as a function of the angle the penetration vector makes with the gravitational vector.

10. The hardness measuring device of claim 4, wherein an adjusting mechanism is associated with the impulse spring, said adjusting mechanism biasing the impulse spring for a specific measuring process, the bias of the impulse spring depends on the orientation of the penetration vector and, independent of the orientation of the penetration vector, the impulse with which the penetration body strikes the workpiece has a prescribed value.

11. The hardness measuring device of claim 1, wherein the mechanical drive is a compression spring, that rests against the housing at one end and is disposed on the penetration body at the other end, the test force with which the penetration body is pressed into the workpiece substantially corresponds to a force with which the compression spring is compressed and the penetration body freely protrudes from the housing in the rest position and in the measuring position.

12. The hardness measuring device of claim 1, wherein the mechanical drive is an electric motor, the electric motor is disposed between the housing and the penetration body.

13. The hardness measuring device of claim 3, further comprising an encoder that senses a deflection of the spring, and wherein the encoder is a Hall probe.

* * * * *